United States Patent [19]

Thiele et al.

[11] Patent Number: 4,462,082
[45] Date of Patent: Jul. 24, 1984

[54] AUTOMATIC CALIBRATION SYSTEM FOR ULTRASONIC INSPECTION

[75] Inventors: Alfred W. Thiele, Canoga Park; Robert E. McLain, Woodland Hills; Modesto T. Martinez, Jr., Duarte; Richard C. Lewis, Santa Monica; Michael S. Kim, Canoga Park, all of Calif.

[73] Assignee: Rockwell International Corporation, El Segundo, Calif.

[21] Appl. No.: 303,230

[22] Filed: Sep. 17, 1981

[51] Int. Cl.³ .................................................. G01N 29/04
[52] U.S. Cl. ............................................ 364/571; 364/507; 367/13; 73/1 DV; 73/620; 73/631
[58] Field of Search ...................... 364/506, 507, 571; 73/1 DV, 618, 620, 621, 624, 625, 631, 641, 627; 367/13, 65

[56] References Cited

U.S. PATENT DOCUMENTS

| | | | |
|---|---|---|---|
| 3,982,425 | 9/1976 | McLain | 364/506 |
| 4,004,454 | 1/1977 | Matay | 73/631 |
| 4,039,767 | 8/1977 | Leschek | 73/1 DV |
| 4,043,181 | 8/1977 | Nigam | 73/631 |
| 4,102,205 | 7/1978 | Pies et al. | 364/506 |
| 4,356,731 | 11/1982 | Mahony | 73/631 |
| 4,391,124 | 7/1983 | Drost et al. | 73/620 |

Primary Examiner—Gary Chin
Attorney, Agent, or Firm—Henry Kolin; Clark E. DeLarvin; H. Fredrick Hamann

[57] ABSTRACT

A method and apparatus is disclosed for calibrating an ultrasonic inspection system having a plurality of transducers (12a, 12b, 12c) coupled by a common amplifier (16) to a distance-amplitude correction (D-AC) circuit comprised of a multiplying digital-to-analog converter (26') which receives, as a function of the transit time of an ultrasonic signal measured by a clock counter (34), a D-AC correction stored in a look-up table in a random access memory (24'). The D-AC correction function stored in the look-up table for each transducer is the inverse of a return signal response curve determined by measuring the peak amplitude of return signals from calibration holes at known depths in a test block (10) while in a calibrate mode, i.e., with a switch (SW) in a state to bypass the MDAC. An equation of a curve that best fits the peak measurements is then found by a digital computer (20) and used to determine the values of points along a curve superimposed on the response curve, except at near field where the calibration system is provided with truncation for near-field effects. Inverse values of these points are then stored in the look-up table for use as correction factors applied to the amplitudes of return signals during an inspection mode of operation. In that way, all return signals from flaws of the same size are caused to have the same amplitude regardless of depth, without the need for utilizing tedious and time-consuming manual calibration methods.

8 Claims, 4 Drawing Figures 4,462,082

AUTOMATIC CALIBRATION SYSTEM FOR ULTRASONIC INSPECTION

BACKGROUND OF THE INVENTION

1. Field of the Invention

This invention relates to apparatus for automated ultrasonic inspection of thick metal sections using an ultrasonic transducer, and more particularly to a method and apparatus for automatic calibration of the sensitivity of the system so that a flaw of constant size produces the same return signal independent of its position, and more importantly independent of its depth.

2. Description of the Prior Art

It is an accepted practice to nondestructively examine metals and other structural materials for flaws using ultrasonic signals. This technique is applied to thick sections that are used in boilers and pressure vessels in accordance with the American Society of Mechanical Engineering (ASME) Boiler and Pressure Vessel Code. The code sets forth the requirements for such examinations.

One of these requirements describes the calibration methods to be used prior to each inspection. A block of sample material, usually taken from the vessel itself during its construction, such as at a location where a passage is cut out to install nozzles through the vessel wall, is provided with three calibration holes drilled into it parallel to the surface at depths of $\frac{1}{4}$, $\frac{1}{2}$ and $\frac{3}{4}$ of the thickness (T) of the sample. The sensitivity of the ultrasonic inspection system is then adjusted as a function of depth so that, for all three of these calibration holes, the same flaw indication signal is produced by the ultrasonic inspection system operating on the sample, nominally 50% of screen height on the instrument. This adjustment is referred to as a Distance-Amplitude Correction (D-AC).

The D-AC capability has heretofore been implemented with a controllable gain amplifier. The amplifier must correct for attenuation due to absorption which is an exponential function, beam spread which is an inverse distance-squared function, near-field effects, and other lesser contributions. The calibration is performed manually by adjusting a number of independent controls, typically from three to six controls, so that the signal from the three calibration holes give return signals at 50% of screen. For example, the gain control terminal of the D-AC amplifier may be connected to an analog exponential function generator synchronized with the round-trip time of the ultrasonic pulses reflected by the calibration holes at $\frac{1}{4}$T, $\frac{1}{2}$T and $\frac{3}{4}$T.

The output of the D-AC amplifier is displayed while the function generator is adjusted to produce a constant amplitude signal for all three calibration holes at 50% of display screen height. This requires at least two adjustments in the exponential function generator to set the starting point and the rate of change of the function, and since the correction function is not a true exponential function, it is necessary to use two exponential function generators, each with the two adjustments just mentioned, and a combining (summing) circuit. The latter requires a fifth adjustment to set the ratio at which the two exponential functions are combined.

In general, the signals from the three holes cannot be displayed on the screen simultaneously, so that the interaction of the multiple adjustments on the return signals from the different holes cannot be seen. As a result, the process requires iteration between the controls and the signals. That is very time consuming (about 25% of total time devoted to inspections) and dependent upon the skill of the operator. Consequently, the procedure is not ordinarily continued once a minimally acceptable result is obtained which satisfies the code requirement.

OBJECTS AND SUMMARY OF THE INVENTION

An object of the present invention is to provide apparatus for deriving a distance-amplitude correction function from test block signals without any requirement of iteration between operator controls and the test block signals.

A further object is to provide apparatus for deriving a distance amplitude correction function in a short time scarcely greater than the time required to obtain one set of test block signals.

Still another object is to provide apparatus for deriving a distance amplitude correction function with a high degree of accuracy independent of any operator skills.

These and other objects of the invention are achieved in an ultrasonic inspection system having a transducer for receiving ultrasonic return signals from calibration holes in a test block and amplifying means with adjustable gain for coupling the transducer to an analog-to-digital converter at the input of a digital computer utilized for processing of inspection data. With the gain of the coupling means at a predetermined value, such as a value that produces a signal that is 50% of full scale for a calibration hole of depth T/2 (where T is the thickness of the test block), the amplitude of the return signals at the output of the amplifying means are measured for test holes at the various depths (T/4, T/2, 3T/4) and converted to digital form. These measurements are stored in the digital computer as three points of a curve. The computer is then used to find a curve defined by an equation which best fits the three points. From this equation the computer calculates the values of a number of points evenly spaced in depth. The reciprocal of these values are applied to ultrasonic return signals from corresponding depths as a correction function to achieve the proper calibration. This correction function is reduced to a look-up table by the computer and stored in a random access memory where the addresses correspond to the argument of the function stored in the table, namely depth measured in round trip transit time. During inspection, a clock counter is synchronized with each ultrasonic pulse transmitted into the material to be inspected to generate addresses for retrieving the values of the correction function to be applied to the ultrasonic return signal in real time, preferably using a multiplying digital-to-analog converter, as the return signal is converted to digital form for processing by the computer means.

The novel features that are considered characteristic of this invention are set forth with particularity in the appended claims. The invention will best be understood from the following description when read in connection with the accompanying drawings.

DESCRIPTION OF PREFERRED EMBODIMENTS

Figure 1:
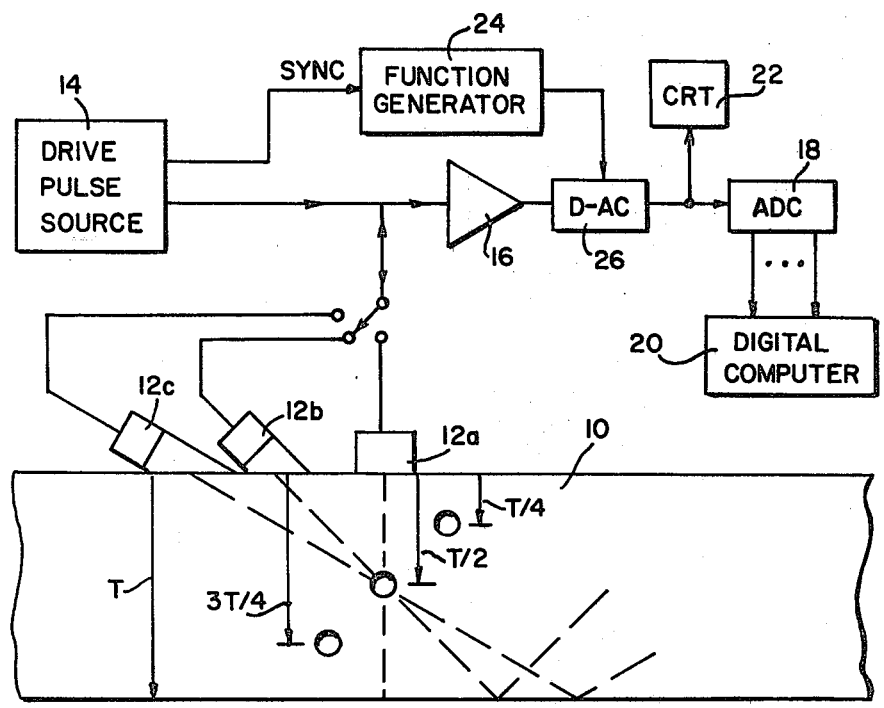
FIG. 1 is a general block diagram of the prior art.

Before proceeding with a description of preferred embodiments of the present invention, the prior art will be described in more detail with reference to FIG. 1, which shows the basic elements of an ultrasonic inspection system on a test block 10 for calibration. The system is comprised of one or more piezoelectric transducers 12a, 12b and 12c carried by a "skate" (not shown) for automated ultrasonic inspection of the wall of a boiler or pressure vessel, as more fully described in U.S. Pat. No. 3,982,425. Each drive pulse from a source 14 excites the transducer 12 to transmit a burst of ultrasonic energy into the material being inspected, which is the test block, during calibration of the ultrasonic inspection system. Bursts of energy reflected from the back surface, or some defect in the path of the transmitted energy, are received by the transducer 12, detected and amplified by an amplifier 16, and converted to digital form by an analog-to-digital converter (ADC) 18 for transfer into a digital computer 20 for analysis. The computer effectively measures the elapsed time, i.e., the transit time between the transmission of an energy burst and the corresponding received signal, and from that determines the distance of any defect along the transmission path in the material. This permits mapping the location of defects.

Information about the sizes of the defects can be derived from the amplitudes of the echo signals, but attenuation of the return signals by the material being inspected must be taken into consideration. To do so requires complex calculations because the attenuation function is a nonlinear function of transmission path length, and more importantly because the attenuation function is accompanied by other factors which decrease signal amplitude, such as beam spread, near-field effects and other lesser contributing factors.

To take those factors into consideration, the inspection system is calibrated in accordance with the ASME code referred to hereinbefore using the block 10 of a material identical to the vessel to be inspected, and of the same thickness. In fact, the practice is to use as a test block a section cut out of the vessel to install nozzles through the vessel wall, as noted hereinbefore. FIG. 1 illustrates such a test block having three test holes drilled through it from one side at locations spaced from the top a distance T/4, T/2 and 3T/4, where T is the thickness of the block. The holes are generally displaced, as shown, in order that an ultrasonic pulse transmitted perpendicularly through the material from a transducer 12a may return a clear echo signal from each of the three holes without the ones at T/4 and T/2 obscuring the return signals from the holes at T/2 and 3T/4.

During inspection, any defects noted are analyzed as to shape, as well as size and location, by "looking" at the defects with energy transmitted along paths at 60° and 45° from perpendicular to the surface, as well as perpendicular to the surface. For that purpose, the additional transducers 12b and 12c are connected to the system through a multiplexer (not shown) each with its own drive pulse source, or pulser. These other "looks" are also repeated from another direction orthogonal to the two looks illustrated in the plane of the drawing. For that purpose, two additional transducers (not shown) are provided. Thus, a total of five transducers are provided, all usually mounted on a single skate, and the calibration procedure, which will now be described, must be repeated for each transducer.

The calibration procedure for each transducer separately consists of observing on a cathode ray tube (CRT) 22 the echo return signals from the three calibration holes in the test block 10, and so adjusting a function generator 24 as to cause it to produce a correction function which, when applied to a distance-amplitude correction (D-AC) circuit 26, will cause the echo return signals from all three calibration holes to appear on the CRT with the same amplitude at 50% of screen height. Heretofore, the D-AC has been implemented with a controllable gain amplifier, and the correction function generator has been implemented with two exponential function generators that are combined as described hereinbefore to produce a composite analog signal that will so control the gain as to correct for attenuation due to absorption (which is an exponential function), beam spread (which is an inverse distance-squared function), near-field effects, and other contributing factors.

Figure 2:
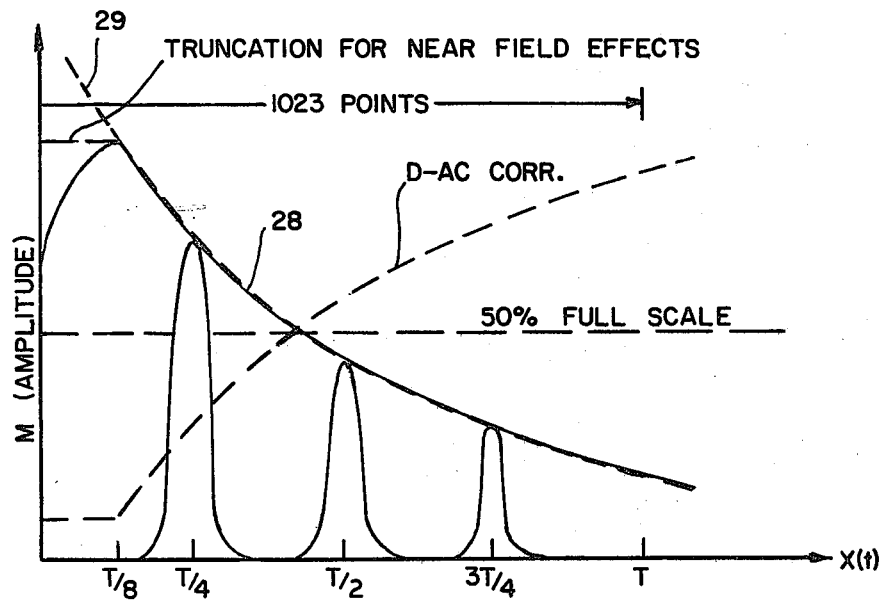
FIG. 2 is a waveform diagram useful in understanding the prior art and the objects of the present invention.

Referring to FIG. 2, the echo return signals from the three calibration holes are shown as they might appear in time sequence if a single ultrasonic burst of energy could be used to produce the respective returns at T/4, T/2 and 3T/4. Since the three calibration holes differ only in their distance from the transducer, it is readily apparent that a response curve 28 fitted to the three return signal peaks defines a response function. If the response function were inverted and applied as the correction to the D-AC, the result would be a uniform height of all three echo return signals on the display screen, though not necessarily at 50% of screen height. The channel gain may have to be adjusted to normalize the return signals so that all points may be correlated to 50% of screen height, such as by adjusting the gain of the amplifier 16.

Complexity in the prior art procedure arises from not only having to adjust two exponential function generators independently while combining them to form the composite analog signal used for correction, as noted hereinbefore, but also from not having all three echo return signals on display at the same time. The latter problem could, perhaps, be overcome by marking the CRT with a grease pencil to provide the three points to which the response function is to be fitted, but still there is the complexity of having a total of about five independent adjustments to be made on the two exponential function generators and combining circuit. Moreover, the correction function must be valid as applied to the system in operation. To assure that, the practice is to make the adjustments in the system manually as the echo return signals are separately displayed on the CRT until all three appear at precisely 50% of the screen height, a process that requires many iterations. The iteration steps of adjusting the controls and viewing the return pulses separately are very time consuming (about 25% of inspection time, depending upon the skill of the operator) and marginally acceptable to the code.

Another problem with the prior art is that it is difficult to maintain the function generator stable for the entire period of the inspection, which may take more than one day. Consequently, although those skilled in the art may readily think of simple circuits for the exponential function generators and a summing circuit, in practice such simple circuits will not provide acceptable correction. The need for a high degree of stability requires complex circuitry with adequate temperature compensation and immunity from variations in power supply, and freedom of drift because of aging of components.

Figure 3:
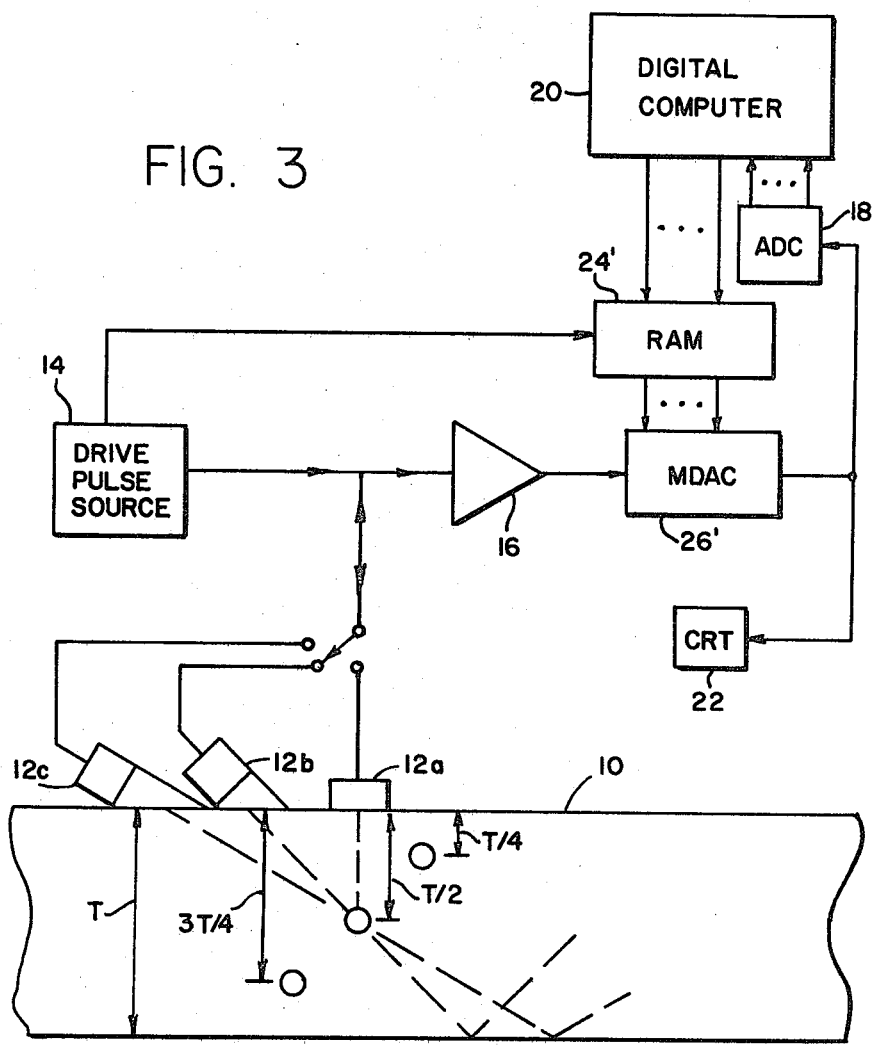
FIG. 3 is a general block diagram of the present invention.

All stability problems, as well as the problem of having to perform time consuming iteration steps in the calibration, are overcome by the present invention, organized as shown in FIG. 3, wherein the D-AC is implemented not as an amplifier having electronic gain control but as a multiplying digital-to-analog converter (MDAC) 26' which receives the correction function in digital form from a table stored in a random access memory (RAM) 24' and in the process of converting that function into an analog signal, multiplies it by an analog return signal to produce a corrected analog return signal. For convenience, the elements corresponding directly to the same elements of the prior art system are identified in FIG. 3 by the same reference numerals as in FIG. 1, with a prime to signify modification or substitution of elments to form the new system.

In operation, the invention organized as shown in FIG. 3 reduces the calibration procedure to an automatic process requiring very little operator attention. The steps are as follows:

1. With the D-AC function held off during the calibration mode of operation, such as by holding the digital input to the MDAC at unity, or simply bypassing the MDAC, the amplitudes of the three calibration holes are detected and stored in the working memory of the digital computer 20'.
2. The computer determines the correction to be applied to the ultrasonic signal return to achieve the proper calibration.
3. The correction function is reduced to a look-up table by the computer and loaded into the random access memory in the D-AC system.
4. The system is placed in an operation mode with the D-AC function on while the skate is still on the test block. The corrected return signal amplitudes of each of the calibration holes are measured to verify that the calibration operation has been performed correctly. The system is then ready for ultrasonic inspection.

This system, which reduces the time required for calibration of an array of ten transducers from about four hours to about thirty minutes, simply requires the operator to properly position the transducer skate over the three holes for each of the transducers in succession, adjust the channel gain for 50% of screen height for a return signal from the calibration hole at T/2, and command the computer to store the peak value of signal return from each calibration hole. To assure that proper positioning has been achieved, the operator views on the CRT 22 the signal return of each transducer as it is positioned for each of the three calibration holes in succession. Once the proper signal return is achieved for each hole, the operator commands the digital computer to store the peak amplitude of the signal return from the hole. The skill of the operator is no longer a factor in the time required, and accuracy is not a function of the time invested.

The digital computer determines the correction to be applied to each of the transducers separately by examining the peak amplitudes of the three return signals received from the three calibration holes. The peak amplitudes of these three signals usually decrease monotonically with depth, i.e., with round trip transmission path length. The equation for a curve 28 (FIG. 2) fit to these three amplitudes can be computed. Since the return signal is being attenuated exponentially, the linearity of the fitting function will be improved by first determining the logarithm of the amplitude. The solution of the coefficients may be achieved by standard mathematical techniques, such as the Gauss-Jordan algorithm, or simply using straight line segments at incremental points along the response curve 28.

This curve 28 can be used to predict the amplitude response of a given flaw anywhere out to the far surface of the material. However, in the near field, which is to a depth of T/8, near-field effects cause an attenuation of the response, as shown by the response curve 28 of FIG. 2, between the origin and T/8. In that near field, the D-AC function necessitates truncation of the D-AC correction, as shown in FIG. 2, so that it is a constant for any flaw between the front surface and T/8. The inverse of this curve is then the correction to be applied to return signals during operation in the inspection mode.

Figure 4:
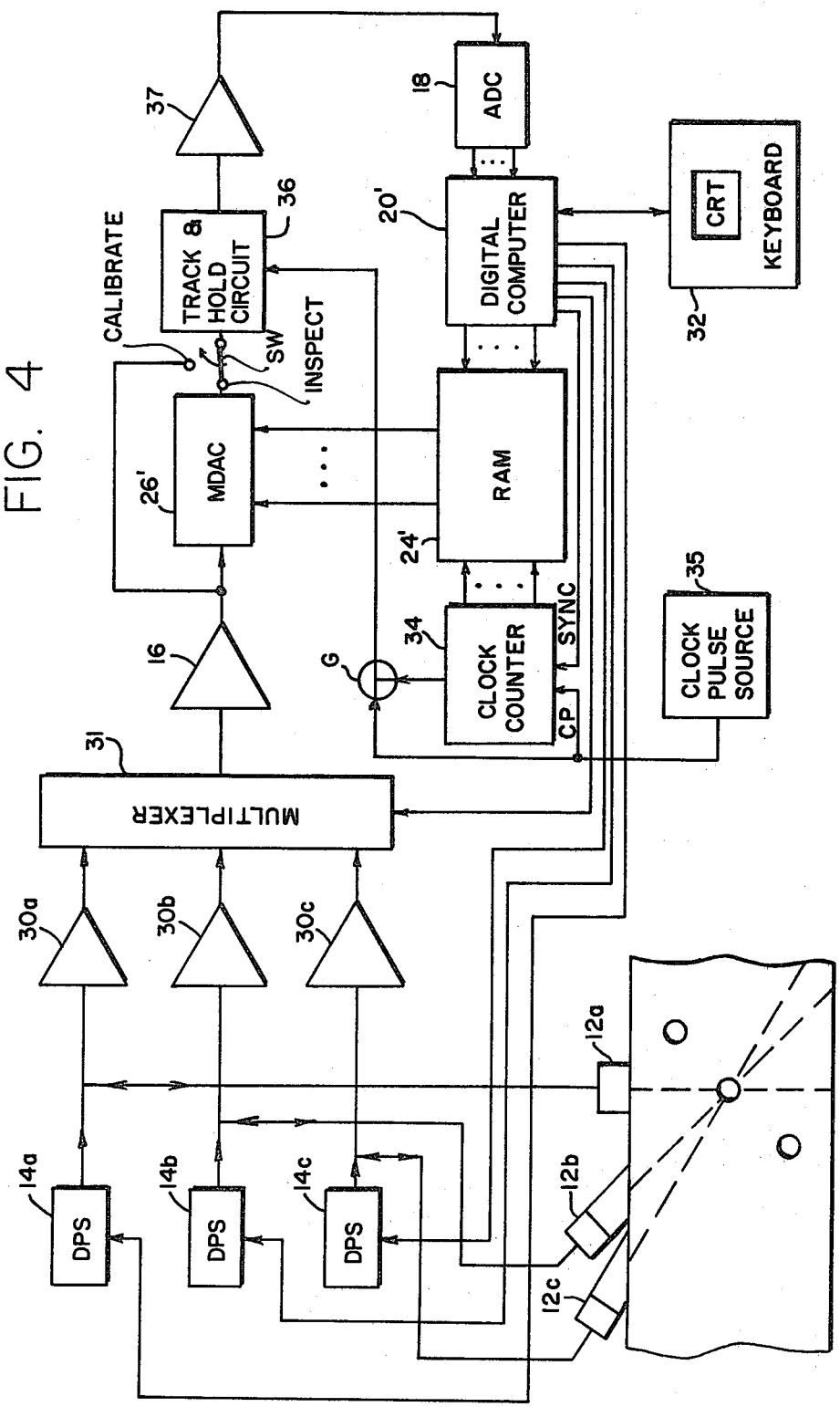
FIG. 4 is a graph useful in understanding the present invention.

A preferred embodiment will now be described with reference to FIG. 4. Again the same reference numerals will be employed to refer to the same elements as in FIG. 3. For simplicity only three transducers are shown, though in practice there will be at least two shear-wave transducers (12b) at 45° oriented to look in orthogonal directions, and two shear-wave transducers (12c) at 60° also oriented to look in orthogonal directions, in addition to at least one L-wave transducer at 0° (i.e., a transducer looking in a direction perpendicular to the block surface). Separate drive pulse sources (DPS: 14a, 14b, 14c) and preamplifiers (30a, 30b, 30c) are provided for each of the transducers to facilitate exciting them in succession. A multiplexer 31 controlled by the digital computer couples one of the preamplifiers at a time to a common amplifier 16. The computer is programmed to interact with the operator by displaying on a CRT at a control console 32 its current status, and advising the operator what commands he should enter through a keyboard at the console for an orderly operation of the system in the calibrate mode, and then the inspection mode. The output of the multiplexer is coupled by the amplifier 16 to the multiplying DAC 26', which is effectively held off by the computer 20' causing the RAM 24' to output a D-AC function value of unity, or by a switch SW in its alternate (calibrate mode) position to bypass the multiplying DAC during the calibration procedure.

With each pulse initiated out of the drive pulse source 14 by the computer, a clock counter 34 is reset to again start counting pulses from a clock pulse source 35. Once the counter starts counting, a gate G is enabled to transmit the clock pulses being gated to a track and hold circuit 36. The leading edge of each clock pulse initiates a hold period in the track and hold circuit 36 so that it will not attempt to track the output signal of the MDAC while a new multiplier is being fetched from the RAM and stored in an input buffer of the MDAC for multiplication of the input analog signal during the remainder of the clock period. Alternatively, the circuit 36 may be a sample and hold, with each sample taken at the leading edge of the clock pulse when switching transients from the last multiplier will have subsided. In this way range gating of the echo return signal could be effected for a synchronous system. Note that the embodiment illustrated is asynchronous, and that the signal applied to the CRT and ADC is a true analog signal, not a stepped signal that approximates the true analog signal as would be the case with a sample and hold circuit.

This analog signal from the track and hold circuit is amplified by a post-amplifier 37 and periodically sampled and converted to digital form by an asynchronous ADC 18. An output buffer of the ADC 18 stores the digital value of the sample while a new sample is being converted. The computer 20' reads into its working memory from the ADC a predetermined number of points equally spaced, such as 1023 points, as shown in FIG. 2. After all points are thus effectively range gated into the computer for a burst of energy, the computer announces to the operator to go to the next transducer, and the procedure is repeated for each of the transducers. The computer meantime analyzes the data for each transducer and finds the peak values for each of the three calibration holes.

Once the peak values are found for all three of the calibration holes for a given transducer, the process may begin for finding the equation that defines a curve that best fits the three points defined by those values. It is then that the correction to be applied during inspection to signals from that transducer is determined as a function of round trip path length, which is a function of time. A table of the corrections as a function of time is stored in the working memory of the computer until the same procedure has been completed for every transducer. All tables (one for each transducer) are then stored in the RAM for access during operation in the inspection mode, in which case the RAM address is comprised of not only the output of the clock counter, but also a transducer identificaion (ID) code from the computer.

Alternatively, as the computer switches from one transducer to the next during the inspection mode, either automatically or under control of the operator, the correction table for that transducer may be loaded into the RAM. This alternative has the advantage of requiring less memory capacity in the RAM, but has the disadvantage of requiring time for loading the RAM as the computer switches from one transducer to the next in the skate for each skate position. It would be preferable to have all correction tables stored in the RAM at all times during the inspection mode so as to quickly cycle through all transducers at each skate position.

For operation of the system in the inspection mode, the switch SW is placed in the position shown, and the skate is moved from the calibration block onto the wall of the boiler or pressure vessel to be inspected. During inspection, the multiplying DAC produces the product of the ultrasonic signal and the correction function to yield a corrected ultrasonic signal at the input of the ADC 18, which may be either a range gated ADC or a transient digitizer. Either type will satisfy the requirement of this system. The output of ADC is read into the computer for later analysis of flaws found in the material being inspected. In that manner, the correction function is applied to an ultrasonic return signal in real time.

An exemplary procedure internal to the computer for fitting a curve to three peak values of a return signal for each transducer will now be described with reference to FIG. 2. Assuming the curve is defined by a quadratic equation of the form:

$$AX^2 + BX + C = M \quad (1)$$

The first step is to set the value of M in this equation to the successive peak values $M_1$, $M_2$ and $M_3$ measured at $X = T/4$, $T/2$ and $3T/4$, respectively. This yields the following set of three equations:

$$A(T/4)^2 + B(T/4) + C = M_1 \quad (2)$$

$$A(T/2)^2 + B(T/2) + C = M_2 \quad (3)$$

$$A(3T/4)^2 + B(3T/4) + C = M_3 \quad (4)$$

The quadratic equation (1) with those values of A, B and C substituted thus defines the precise dotted-line curve 29 shown in FIG. 2, which is superimposed on the response curve 28. That equation can then be solved for all values of X from T/8 to T, i.e., from time $t = \frac{1}{8}$ to a maximum, where t is the round trip transit time from the transducer to the far wall and back. (Note that for shear-wave transducers there is no reflection directly back from the far wall, but only reflections from flaws between the transducer and the far wall, but range gating permits exclusion of any reflections beyond that limit of interest.) The increments of X at which the equation is solved is set to correspond to the increments of time that the output of the ADC is range gated into the computer, such as 1023 increments over the time span shown in FIG. 2. Note that this time span includes the truncated period from 0 to T/8. The reciprocal of those values of M are the correction values stored as a discrete table. The reciprocal of the value of M is taken as the correction for each increment of X so that it is a multiplicative correction factor that may be applied as the digital input to the multiplying DAC where the digital value is multiplied by the analog input signal in the process of being converted to analog form.

Although particular embodiments of the invention have been described and illustrated herein, it is recognized that modifications and variations may readily occur to those skilled in the art. Consequently, it is intended that the claims be interpreted to cover such modifications and equivalents.

What is claimed is:

1. A method for calibrating the sensitivity of an ultrasonic system for nondestructive inspection of structural material so that a flaw produces a return signal of the same amplitude independent of the depth of the flaw in the material, comprising the steps of
    receiving ultrasonic return signals from calibration holes at known depths in a test block of the material with said system in a calibration mode in which no calibrating correction is applied to ultrasonic return signals and measuring said return signals for peak amplitudes,
    storing said peak amplitudes of said signals returned from said calibration holes separately while in said calibration mode,
    determining from said peak amplitudes and known depths of said calibration holes, an equation for a signal amplitude curve as a function of depth that best fits the measured peak amplitudes,
    determining a set of values from said equation for a number of evenly spaced points over a predetermined range of depths through the test block, and
    applying the reciprocals of said values to ultrasonic return signals from corresponding depths as correction functions during nondestructive inspection of the structural material.

2. A method as defined in claim 1 wherein the correction functions are reduced to a look-up table with transit time as a measure of depth and transit time is measured during operation of said system in an inspection mode for real time application of correction functions to ultrasonic return signals.

3. A method as defined in claim 2 wherein the correction functions are read from the look-up table and applied to an ultrasonic return signal during inspection in real time by counting clock pulses to measure transit time, and multiplying the ultrasonic return signal with each correction function read from the look-up table corresponding to that transit time.

4. A method as defined in claims 1, 2 or 3 wherein a plurality of ultrasonic transducer channels are calibrated by making measurements of said peak amplitudes for said calibration holes for each channel in succession, and storing all of said peak amplitudes for determining said equation for each channel separately, and from said equation for each channel, determining said values and the reciprocals of said values for application as the correction functions for the channel during inspection.

5. Apparatus for calibrating with a test block having holes at known depths, the sensitivity of an ultrasonic system for nondestructive inspection of structural material so that a flaw produces a return signal of the same amplitude independent of its depth in the material, comprising means for receiving ultrasonic return signals from said calibration holes in said test block of the material with said system in a calibration mode during which no calibrating correction is applied to ultrasonic return signals, means for storing as a function of transit time peak amplitudes of said return signals returned from said calibration holes separately while in said calibration mode, means for determining the equation of a signal amplitude curve as a function of transit time that best fits said peak amplitudes and known depths of said calibration holes, means for determining a set of values from said equation for a number of evenly spaced points over a predetermined range of depths through said test block, and means for applying the reciprocals of said values to ultrasonic return signals from corresponding depths as correction functions to ultrasonic return signals during nondestructive inspection of the structural material.

6. Apparatus as defined in claim 5 including a random access memory and means for reducing said correction functions to a look-up table with transit time as a measure of depth for an address and storing said table in said random access memory, and further including means for measuring transit time during operation of said system in an inspection mode for addressing said memory to obtain a correction function corresponding to the measured transit time for application to a return signal in real time.

7. Apparatus as defined in claim 6, including multiplying means, wherein correction functions obtained from said look-up table in said random access memory are applied to an ultrasonic return signal during inspection in real time by said multiplying means multiplying the ultrasonic return signal with the correction function corresponding to the transit time measured.

8. The apparatus as defined in claim 7 wherein said multiplying means is a multiplying digital-to-analog converter.

* * * * *